United States Patent
Barron et al.

(10) Patent No.: US 7,491,376 B2
(45) Date of Patent: Feb. 17, 2009

(54) CHEMICAL DERIVATIZATION OF SILICA COATED FULLERENES AND USE OF DERIVATIZED SILICA COATED FULLERENES

(75) Inventors: Andrew R. Barron, Houston, TX (US); Dennis J. Flood, Oberlin, OH (US); Andrew A. Guzelian, Belmont, MA (US)

(73) Assignee: NewCyte, Inc., Sudbury, MA (US)

( * ) Notice: Subject to any disclaimer, the term of this patent is extended or adjusted under 35 U.S.C. 154(b) by 266 days.

(21) Appl. No.: 11/451,110

(22) Filed: Jun. 12, 2006

(65) Prior Publication Data

US 2008/0233040 A1    Sep. 25, 2008

(51) Int. Cl.
C01B 31/00    (2006.01)

(52) U.S. Cl. .................. 423/445 B; 423/335; 423/460; 423/DIG. 39; 423/DIG. 40; 977/734; 977/735; 977/742

(58) Field of Classification Search .................. 423/335, 423/445 B, 460, DIG. 39, DIG. 40; 977/734, 977/735, 742
See application file for complete search history.

(56) References Cited

U.S. PATENT DOCUMENTS

| | | | |
|---|---|---|---|
| 5,274,018 | A | 12/1993 | Tanaka et al. |
| 5,308,661 | A | 5/1994 | Feng et al. |
| 5,908,585 | A | 6/1999 | Shibuta et al. |
| 6,203,814 | B1 | 3/2001 | Fisher et al. |
| 6,207,229 | B1 | 3/2001 | Bawendi et al. |
| 6,333,598 | B1 | 12/2001 | Hsu et al. |
| 6,559,375 | B1 | 5/2003 | Meissner et al. |
| 6,645,455 | B2 | 11/2003 | Margrave et al. |
| 6,683,783 | B1 | 1/2004 | Smalley et al. |
| 6,835,366 | B1 | 12/2004 | Margrave et al. |
| 6,841,139 | B2 | 1/2005 | Margrave et al. |
| 6,875,412 | B2 | 4/2005 | Margrave et al. |
| 6,918,946 | B2 | 7/2005 | Korgel et al. |
| 6,946,597 | B2 | 9/2005 | Sager et al. |
| 6,969,897 | B2 | 11/2005 | Kim, II |
| 7,253,014 | B2 | 8/2007 | Barron et al. |
| 2001/0024078 | A1 | 9/2001 | Dimitrijevic et al. |
| 2001/0031900 | A1 | 10/2001 | Margrave et al. |
| 2001/0041160 | A1 | 11/2001 | Margrave et al. |
| 2002/0004028 | A1 | 1/2002 | Margrave et al. |
| 2002/0076846 | A1 | 6/2002 | Ihm |
| 2002/0084504 | A1 | 7/2002 | Narayan |
| 2002/0086124 | A1 | 7/2002 | Margrave et al. |
| 2002/0094699 | A1 | 7/2002 | Houng et al. |
| 2002/0110513 | A1 | 8/2002 | Margrave et al. |
| 2003/0065206 | A1* | 4/2003 | Bolskar et al. .............. 558/87 |
| 2004/0265209 | A1 | 12/2004 | Colbert et al. |
| 2007/0098621 | A1 | 5/2007 | Margrave et al. |
| 2008/0023067 | A1 | 1/2008 | Hu et al. |

FOREIGN PATENT DOCUMENTS

| | | |
|---|---|---|
| WO | WO-2003043934 A1 | 5/2003 |
| WO | WO-2004046023 A2 | 6/2004 |
| WO | WO-2005/000735 A2 | 1/2005 |

OTHER PUBLICATIONS

Barron et al. "Silica Coated Single Walled Carbon Nanotubes" Nano Letters, Apr. 24, 2003.*
Loscutova, Ryan et al. "Coating single-wlled carbon nanotubes with cadmium chalcogenides" © The Royal Society of Chemistry 2005, www.rsc.org/materials, Journal of Materials Chemistry, 2005, vol. 15, pp. 4346-4353, Aug. 23, 2005.
Seeger et al., SiOx-Coating of carbon nanotubes at room temperature, May 4, 2001, Chem. Phys. Letters 339, pp. 41-46.
Hiura Hidefumi, JP 08-325195, "Metal-Coated Carbon Nanotube and its Production", published Oct. 12, 1996, Patent Abstracts of Japan, (Machine Translation).

* cited by examiner

*Primary Examiner*—Erin Barry Saad
*Assistant Examiner*—Erin P Barry
(74) *Attorney, Agent, or Firm*—Nutter McClennen & Fish LLP; Reza Mollaaghababa; Joshua T. Matt

(57) ABSTRACT

This invention is directed to a new composition of matter in the form of chemically derivatized silica coated fullerenes, including silica coated $C_{60}$ molecules and silica coated carbon nanotubes, processes for making the same and to uses for the derivatized silica coated fullerenes. Included among many uses in chemical, physical or biological fields of use, but not limited thereto, are high speed, low loss electrical interconnects for nanoscale electronic devices, components and circuits. In one embodiment, this invention also provides a method for preparing silica coated fullerenes having substituents attached to the surface of silica coated fullerenes by reacting silica coated fullerenes with a wide range of organic or inorganic chemical species in a gaseous or liquid state. Preferred substituents include but are not limited to organic groups and organic groups containing heteroatoms such as oxygen, nitrogen, sulfur, and halogens. The identity of the surface functional group is chosen to provide desirable properties to the silica coated fullerenes including but not limited to solubility, miscibility, stickiness, and melting point. The present invention also describes the application of surface functionalized silica coated fullerenes as components of polymer blends and composites.

11 Claims, No Drawings

CHEMICAL DERIVATIZATION OF SILICA COATED FULLERENES AND USE OF DERIVATIZED SILICA COATED FULLERENES

STATEMENT REGARDING FEDERALLY FUNDED RESEARCH OR DEVELOPMENT

Not Applicable.

FIELD OF THE INVENTION

This invention is directed to derivatizing the surface of silica coated fullerenes, including derivatizing the surface of silica coated C60 molecules and sidewall or endcaps of silica coated carbon nanotubes, and to uses for the derivatized fullerenes, including dispersing derivatized silica coated fullerenes in various solutions containing a wide range of organic or inorganic chemical species.

BACKGROUND OF THE INVENTION

As used herein, fullerene is any carbonaceous material wherein the structure is a regular, three dimensional network of fused carbon rings arranged in any one of a number of possible structures including, but not limited to, cylindrical, spherical, ovoid, oblate or oblong. Common fullerenes include the cylindrical carbon nanotube and the icosahedral $C_{60}$ carbon molecules. In particular, the fullerene is preferably selected from the group consisting of $C_{60}$, $C_{72}$, $C_{84}$, $C_{96}$, $C_{108}$, $C_{120}$, single-walled carbon nanotubes (SWNT) and multi-walled carbon nanotubes (MWNT).

Derivatization of planar and other macroscopic silica surfaces is well known and in the public domain. Silica coated fullerenes, including silica coated single walled or multi-walled carbon nanotubes (s-SWNT or s-MWNT) and silica coated $C_{60}$ molecules, have been made by the process described in US/PCT Application 20,050,089,684 entitled "Coated Fullerenes, Composites and Dielectrics made Therefrom." Since the discovery of silica coated fullerenes in 2002 researchers have been searching for ways to manipulate them chemically. While there have been many reports and review articles on the production and physical properties of chemically functionalized fullerenes and in particular carbon nanotubes, reports on chemical manipulation of silica coated fullerenes, including silica coated $C_{60}$ molecules and silica coated carbon nanotubes, have been non-existent.

Single walled carbon nanotubes and multiwalled carbon nanotubes are elongated members of the fullerene family. Since their discovery they have come under intense multidisciplinary study because of their unique physical and chemical properties and their possible applications. Single walled carbon nanotubes can be either metallic or semiconducting, depending on their helicity and diameter. More importantly it has been shown that these properties are sensitive to the surrounding environments. For example, the presence of $O_2$, $NH_3$ and many other molecules can either donate or accept electrons and alter the overall conductivity of the single walled carbon nanotubes. Such properties make single walled carbon nanotubes ideal for nanoscale sensing materials. Nanotube field effect transistors have already been demonstrated as gas sensors. However, to introduce selectivity to nanotube sensors, certain functional groups that can selectively bind to specific target molecules need to be anchored on the nanotube surface. Unfortunately, functionalization changes the electronic properties from semiconductor or conductor to insulating, and at present chemical functionalization is not regiospecific. A further major obstacle to such efforts has been diversity of tube diameters, chiral angles, and aggregation states of the tubes. Aggregation is particularly problematic because the highly polarizable, smooth sided single walled carbon nanotubes readily form bundles or ropes with van der Waals binding energy of ca. 500 eV per micrometer of tube contact. This bundling perturbs the electronic structure of the tubes and precludes the separation of single walled carbon nanotubes by size or type; it also precludes the use of single walled carbon nanotubes as individual tubes in any matrix or solvent.

Individual single walled carbon nanotubes may be obtained encased in a cylindrical micelle, by ultrasonically agitating an aqueous dispersion of raw single walled carbon nanotubes in a suitable surfactant. However, upon drying or attempting to incorporate into other solvents or matrices bundles re-form. Single walled carbon nanotubes have been encased in a wide range of organic materials. It would be desirable to fabricate individually coated single walled carbon nanotubes where the coating is retained in solution and the solid state. Of particular interest are dielectric materials such as silica, which may also be compatible with composite matrix materials. Thick coatings of $SiO_2$ on multi walled carbon nanotubes has been reported, while thin layers have been reported on single walled carbon nanotubes. Experimental measurements and theoretical calculations have shown that the silica-coated nanotubes retain the electronic and optical properties of the uncoated nanotubes. The silica coating does not interfere with the properties of the nanotube. However, while these routes allow for isolation of individual nanotubes the surfaces are defined by the surface chemistry of the silica coating. Oxide and hydroxide generally terminate the surface of silica groups. This is a severe limitation on the application of such materials.

SUMMARY OF THE INVENTION

Accordingly, it is an object of this invention to provide a method for derivatizing silica coated fullerenes and in particular silica coated $C_{60}$ molecules and the sidewall and/or endcaps of silica coated carbon nanotubes. It is another object of this invention to provide for dispersions of functionalized silica coated fullerenes that can serve as nucleation sites or binders in various solutions of a wide range of inorganic or organic chemicals. It is yet another object of this invention to provide a silica based substrate for creating nanometer scale catalytic particles using a wide variety of organic or inorganic chemical species. These and other objects of this invention are met by one or more of the following embodiments.

This invention provides a new composition of matter comprised of silica coated fullerenes, including silica coated $C_{60}$ molecules and tubular silica coated carbon molecules derivatized with substituents that are covalently or physically bonded to silicon or oxygen atoms of the surface of the silica coated $C_{60}$ molecules or the side wall or endcaps of the silica coated nanotubes. The resulting composition of matter allows for designed physical properties and compatabilities without altering the electronic and physical properties of the fullerene contained therein. The substituents may in principle be attached on the exterior of the silica coating on the $C_{60}$ molecules. The substituents also may in principle be attached on the longest dimension of the silica coated carbon nanotube. That is the silica that is above the sidewall of the carbon nanotube. Alternatively, the silica can be functionalized on the shortest dimension as defined by the endcaps of the underlying carbon nanotube. The chemically functionalized silica coated fullerenes may have substituents selected from a wide range of organic or inorganic chemical species attached to the surface. Such fullerenes can demonstrate selectable properties that are distinct from the fullerene or the silica coating.

This invention also provides a method for derivatizing silica coated fullerenes comprising reacting silica coated fullerenes with a wide range of organic or inorganic chemical species in gaseous or liquid form. Where the fullerenes are silica-coated fullerenes, and the reaction temperature is between −78° C. and 500° C., the product will be silica coated fullerenes derivatized with a wide range of organic or inorganic chemical species.

This invention also provides a process for preparing a suspension or solution of silica coated carbon nanotubes in a solvent of choice, from which individual silica coated carbon nanotubes may then be isolated, the process comprising providing a mass of silica coated carbon nanotubes that have no van der Waals forces holding them in bundles, unlike the case for uncoated carbon nanotubes or chemically functionalized carbon nanotubes. Derivatizing the sidewall or endcaps of the silica coated carbon nanotubes with a plurality of chemical moieties distributed substantially uniformly along the length of said silica coated carbon nanotube sidewall, said chemical moieties having chemical and steric properties sufficient to prevent the reassembly of van der Waals force bound bundles, produces true solutions and enables recovering the individual, derivatized silica coated carbon nanotubes from said solution or suspension.

In another embodiment, this invention provides a method for forming a dispersion of chemically functionalized silica coated fullerenes in a solvent or polymer. In a particular embodiment chemically functionalized silica coated fullerenes are added to a polymer solution to alter the viscosity or other property of the polymer solution.

DETAILED DESCRIPTION OF THE INVENTION

This invention discloses, in one aspect, a method of making a chemically derivatized, silica coated fullerene comprising a layer of silica covering at least a portion of at least one surface of a fullerene wherein the method comprises (a) dispersing fullerenes with at least a portion of the fullerene surface covered by a layer of silica; and (b) reacting the silica coated fullerene with a derivatizing agent.

As used herein, fullerene is any carbonaceous material wherein the structure is a regular, three dimensional network of fused carbon rings arranged in any one of a number of possible structures including, but not limited to, cylindrical, spherical, ovoid, oblate or oblong. Common fullerenes include the cylindrical carbon nanotube and the icosohedral $C_{60}$ carbon molecules.

In another aspect, the present invention discloses a chemically derivatized, silica coated fullerene comprising a derivatizing agent attached to a silica coating on a fullerene wherein the derivatizing agent is from the functional group consisting of a wide range of organic or inorganic chemical species.

EXAMPLES

The following examples are presented to illustrate the ease and versatility of the approach and are not to be construed as the only examples of the proposed approach or as limiting the scope of the present invention. It is understood that a practitioner, of ordinary skill in the art, will be able to employ alternative reagents and coatings to achieve similar results. Examples of conditions that may be varied include, but are not limited to, choice of silanizing reagent, concentration of silanizing reagent, concentration of carbon nanotubes, reaction solvent, sonication treatment, and post-reaction heat treatments, both in solution and on dry samples.

Example 1

30 mg of silica-coated SWNTs were added to 2 ml of toluene in a test tube. The mixture was sonicated using a horn sonicator for 5 minutes and then stirred under flowing nitrogen. 0.7 ml of aminotriethoxysilane was added, the mixture was sonicated using a horn sonicator for 5 minutes, and stirred for 2 hours under a nitrogen atmosphere. Toluene was added to a total volume of 10 ml and the solution was centrifuged, giving a black precipitate and clear supernatant. The supernatant was discarded and the precipitate was washed with 10 ml of toluene. The centrifugation and washing steps were repeated two additional times. Washing and centrifugation steps were then carried out with 10 ml of ethanol and repeated two additional times.

Example 2

30 mg of silica-coated SWNTs were added to 2 ml of toluene in a test tube. The mixture was sonicated in a water bath for 5 minutes and then stirred under flowing nitrogen. 0.7 ml of aminotriethoxysilane was added, the mixture was sonicated in a water bath for 5 minutes, and stirred for 2 hours under a nitrogen atmosphere. Toluene was added to a total volume of 10 ml and the solution was centrifuged, giving a black precipitate and clear supernatant. The supernatant was discarded and the precipitate was washed with 10 ml of toluene. The centrifugation and washing steps were repeated two additional times. Washing and centrifugation steps were then carried out with 10 ml of ethanol and repeated two additional times.

Example 3

30 mg of silica-coated SWNTs were added to 1 ml of toluene in a test tube. The mixture was sonicated using a horn sonicator for 5 minutes and then stirred under flowing nitrogen. 1.5 ml of aminotriethoxysilane was added, the mixture was sonicated using a horn sonicator for 5 minutes, and stirred for 2 hours under a nitrogen atmosphere. Toluene was added to a total volume of 10 ml and the solution was centrifuged, giving a black precipitate and clear supernatant. The supernatant was discarded and the precipitate was washed with 10 ml of toluene. The centrifugation and washing steps were repeated two additional times. Washing and centrifugation steps were then carried out with 10 ml of ethanol and repeated two additional times.

Example 4

30 mg of silica-coated SWNTs were added to 1 ml of ethanol in a test tube. The mixture was sonicated using a horn sonicator for 5 minutes and then stirred under flowing nitrogen. 1.5 ml of aminotriethoxysilane was added, the mixture was sonicated using a horn sonicator for 5 minutes, and stirred for 2 hours under a nitrogen atmosphere. Ethanol was added to a total volume of 10 ml and the solution was centrifuged, giving a black precipitate and clear supernatant. The supernatant was discarded and the precipitate was washed with 10 ml of ethanol. The centrifugation and washing steps were repeated two additional times.

Example 5

30 mg of silica-coated SWNTs were added to 1 ml of toluene in a test tube. The mixture was sonicated using a horn sonicator for 5 minutes and then stirred under flowing nitrogen. 1.5 ml of octadecyltrichlorosilane was added, the mixture was sonicated using a horn sonicator for 5 minutes, and stirred for 2 hours under a nitrogen atmosphere. Toluene was added to a total volume of 10 ml and the solution was centrifuged, giving a black precipitate and clear supernatant. The supernatant was discarded and the precipitate was washed with 10 ml of toluene. The centrifugation and washing steps were repeated two additional times. Washing and centrifugation steps were then carried out with 10 ml of ethanol and repeated two additional times.

Example 6

30 mg of silica-coated SWNTs were added to 2 ml of toluene in a test tube. The mixture was sonicated using a horn sonicator for 5 minutes and then stirred under flowing nitrogen. 0.7 ml of octadecyltrichlorosilane was added, the mixture was sonicated using a horn sonicator for 5 minutes, and stirred for 2 hours under a nitrogen atmosphere. Toluene was added to a total volume of 10 ml and the solution was centrifuged, giving a black precipitate and clear supernatant. The supernatant was discarded and the precipitate was washed with 10 ml of toluene. The centrifugation and washing steps were repeated two additional times. Washing and centrifugation steps were then carried out with 10 ml of ethanol and repeated two additional times.

Example 7

30 mg of silica-coated SWNTs were added to 1 ml of toluene in a test tube. The mixture was sonicated using a horn sonicator for 5 minutes and then stirred under flowing nitrogen. 1.5 ml of octadecyltrichlorosilane was added, the mixture was sonicated using a horn sonicator for 5 minutes, and stirred for 2 hours under a nitrogen atmosphere. Toluene was added to a total volume of 10 ml and the solution was heated at 70° C. for 1 hour with stirring. The solution was then centrifuged, giving a black precipitate and clear supernatant. The supernatant was discarded and the precipitate was washed with 10 ml of toluene. The centrifugation and washing steps were repeated two additional times. Washing and centrifugation steps were then carried out with 10 ml of ethanol and repeated two additional times.

Example 8

30 mg of silica-coated SWNTs were added to 2 ml of toluene in a test tube. The mixture was sonicated using a horn sonicator for 5 minutes and then stirred under flowing nitrogen. 0.7 ml of octadecyltrichlorosilane was added, the mixture was sonicated using a horn sonicator for 5 minutes, and stirred for 2 hours under a nitrogen atmosphere. Toluene was added to a total volume of 10 ml and the solution was heated at 70° C. for 1 hour with stirring. The solution was then centrifuged, giving a black precipitate and clear supernatant. The supernatant was discarded and the precipitate was washed with 10 ml of toluene. The centrifugation and washing steps were repeated two additional times. Washing and centrifugation steps were then carried out with 10 ml of ethanol and repeated two additional times.

Example 9

30 mg of silica-coated SWNTs were added to 2 ml of toluene in a test tube. The mixture was sonicated using a horn sonicator for 5 minutes and then stirred under flowing nitrogen. 0.7 ml of 2-[methoxy(polyethyleneoxy)propyl]trimethoxysilane was added, the mixture was sonicated using a horn sonicator for 5 minutes, and stirred for 2 hours under a nitrogen atmosphere. Toluene was added to a total volume of 10 ml and the solution was centrifuged, giving a black precipitate and clear supernatant. The supernatant was discarded and the precipitate was washed with 10 ml of toluene. The centrifugation and washing steps were repeated two additional times. Washing and centrifugation steps were then carried out with 10 ml of ethanol and repeated two additional times.

Example 10

30 mg of silica-coated SWNTs were added to 2 ml of ethanol in a test tube. The mixture was sonicated using a horn sonicator for 5 minutes and then stirred under flowing nitrogen. 0.7 ml of 2-[methoxy(polyethyleneoxy)propyl]trimethoxysilane was added, the mixture was sonicated using a horn sonicator for 5 minutes, and stirred for 2 hours under a nitrogen atmosphere. Ethanol was added to a total volume of 10 ml and the solution was centrifuged, giving a black precipitate and clear supernatant. The supernatant was discarded and the precipitate was washed with 10 ml of ethanol. The centrifugation and washing steps were repeated two additional times.

Example 11

30 mg of silica-coated SWNTs were added to 1 ml of toluene in a test tube. The mixture was sonicated using a horn sonicator for 5 minutes and then stirred under flowing nitrogen. 1.5 ml of 2-[methoxy(polyethyleneoxy)propyl]trimethoxysilane was added, the mixture was sonicated using a horn sonicator for 5 minutes, and stirred for 2 hours under a nitrogen atmosphere. Toluene was added to a total volume of 10 ml and the solution was heated at 70° C. for 1 hour with stirring. The solution was then centrifuged, giving a black precipitate and clear supernatant. The supernatant was discarded and the precipitate was washed with 10 ml of toluene. The centrifugation and washing steps were repeated two additional times. Washing and centrifugation steps were then carried out with 10 ml of ethanol and repeated two additional times.

Example 12

30 mg of silica-coated SWNTs were added to 1 ml of ethanol in a test tube. The mixture was sonicated using a horn sonicator for 5 minutes and then stirred under flowing nitrogen. 1.5 ml of 2-[methoxy(polyethyleneoxy)propyl]trimethoxysilane was added, the mixture was sonicated using a horn sonicator for 5 minutes, and stirred for 2 hours under a nitrogen atmosphere. Ethanol was added to a total volume of 10 ml and the solution was heated at 50° C. for 1 hour with stirring. The solution was then centrifuged, giving a black precipitate and clear supernatant. The supernatant was discarded and the precipitate was washed with 10 ml of ethanol. The centrifugation and washing steps were repeated two additional times.

What is claimed is:

1. A method for derivatizing the surface of a silica coated fullerene, including the surface of a silica coated $C_{60}$ molecule and sidewall or endcaps of silica coated carbon nanotubes comprising: (i) reacting silica coated fullerenes, including silica coated $C_{60}$ molecules and silica coated carbon nanotubes, with a derivatizing agent, and (ii) producing derivatized silica coated fullerenes, including derivatized silica coated $C_{60}$ molecules and derivatized sidewalls or endcaps of silica coated carbon nanotubes, wherein the silica coated carbon nanotubes generally have a length from about 5 nm to greater than 1000 nm.

2. A method for derivatizing the surface of a silica coated fullerene including the surface of a silica coated $C_{60}$ molecule and the sidewall or endcaps of a silica coated carbon nanotube comprising reacting the silica coated fullerene, including silica coated $C_{60}$ molecules and silica coated carbon nanotubes, with a derivatizing agent.

3. The method of claim 2, wherein the derivatizing agent is selected from the functional group consisting of a wide range of organic or inorganic chemical species.

4. The method of claim 3, wherein the functional group is an organic group.

5. The method of claim 4, wherein the organic group contains an aliphatic or aromatic hydrocarbon.

6. The method of claim 5, wherein the organic group contains a heteroatom containing functional group.

7. The method of claim 5, wherein the heteroatom is chosen from oxygen, nitrogen, boron, sulfur, a halogen, silicon, phosphorus, or a metal atom.

8. The method of claim 3, wherein the silica coated fullerene, including silica coated $C_{60}$ molecules and silica coated carbon nanotubes, is reacted with the derivatizing agent at a reaction temperature between about −78° C. and about 500° C.

9. The method of claim 4, wherein the silica coated fullerene, including silica coated $C_{60}$ molecules and silica coated carbon nanotubes, is reacted with the derivatizing agent at a reaction temperature between about −10° C. and 100° C.

10. A method for derivatizing the surface of a silica coated fullerene, including the surface of a silica coated $C_{60}$ molecule and the sidewall or endcaps of silica coated carbon nanotubes comprising: (i) selecting a derivatizing agent; and (ii) reacting the silica coated fullerenes with the derivatizing agent at a suitable reaction temperature in a suitable solvent or matrix.

11. The method of claim 10, wherein the solvent is the derivatizing agent.

* * * * *